(12) United States Patent
Fischer (10) Patent No.: US 8,569,073 B2
(45) Date of Patent: Oct. 29, 2013

(54) TEST ELEMENT HAVING COMBINED CONTROL AND CALIBRATION ZONE

(75) Inventor: Thomas Fischer, Rauenberg (DE)

(73) Assignee: Roche Diagnostics Operations Inc., Indianapolis, IN (US)

(*) Notice: Subject to any disclaimer, the term of this patent is extended or adjusted under 35 U.S.C. 154(b) by 158 days.

(21) Appl. No.: 13/132,624

(22) PCT Filed: Dec. 2, 2009

(86) PCT No.: PCT/EP2009/008571
§ 371 (c)(1),
(2), (4) Date: Jun. 3, 2011

(87) PCT Pub. No.: WO2010/063456
PCT Pub. Date: Jun. 10, 2010

(65) Prior Publication Data
US 2011/0244598 A1    Oct. 6, 2011

(30) Foreign Application Priority Data
Dec. 3, 2008 (EP) .................................... 08020964

(51) Int. Cl.
*G01N 33/558* (2006.01)
*G01N 33/544* (2006.01)
*G01N 33/545* (2006.01)

(52) U.S. Cl.
USPC ........................... 436/514; 436/530; 436/531

(58) Field of Classification Search
USPC ......................................... 436/514, 530, 531
See application file for complete search history.

(56) References Cited

U.S. PATENT DOCUMENTS

| | | |
|---|---|---|
| 4,168,146 A | 9/1979 | Grubb et al. |
| 4,235,601 A | 11/1980 | Deutsch et al. |
| 4,366,241 A | 12/1982 | Tom et al. |
| 4,442,204 A | 4/1984 | Greenquist et al. |
| 4,861,711 A | 8/1989 | Friesen et al. |
| 5,028,535 A | 7/1991 | Buechler et al. |
| 5,073,484 A | 12/1991 | Swanson et al. |
| 5,141,850 A | 8/1992 | Cole et al. |
| 5,395,754 A * | 3/1995 | Lambotte et al. .............. 435/7.4 |
| 5,458,852 A | 10/1995 | Buechler |
| 5,591,645 A | 1/1997 | Rosenstein |
| 5,726,064 A * | 3/1998 | Robinson et al. ............. 436/514 |
| 6,506,612 B2 | 1/2003 | Kang et al. |

(Continued)

FOREIGN PATENT DOCUMENTS

| | | |
|---|---|---|
| EP | 0291194 | 11/1988 |
| EP | 0253464 B1 * | 5/1992 |

(Continued)

*Primary Examiner* — Shafiqul Haq
*Assistant Examiner* — Gary E Hollinden
(74) *Attorney, Agent, or Firm* — McDonnell Boehnen Hulbert & Berghoff LLP (57) ABSTRACT

A test element, for example in the form of an immunological test strip functioning according to the sandwich principle, for the fluorophoric detection of one or more analytes in a sample comprising an analyte detection zone and a combined control and calibration zone. The combined control and calibration zone include a fluorophore and binding partners for the specific binding of reagents labelled with a fluorophore. Furthermore, the invention concerns a method for calibrating an analyte-specific measurement signal, a method for determining the concentration of an analyte in a sample and the use of the test element for calibrating a signal generated in the analyte detection zone of a test element.

12 Claims, 3 Drawing Sheets

(56) References Cited

U.S. PATENT DOCUMENTS

| | | | |
|---|---|---|---|
| 6,573,108 B1* | 6/2003 | Hardman et al. | 436/518 |
| 7,659,086 B2* | 2/2010 | Harris et al. | 435/7.9 |
| 2002/0001852 A1* | 1/2002 | Mendel-Hartvig et al. | 436/514 |
| 2003/0119203 A1* | 6/2003 | Wei et al. | 436/514 |
| 2003/0119204 A1* | 6/2003 | Wei et al. | 436/514 |
| 2004/0126767 A1 | 7/2004 | Anderberg et al. | |
| 2005/0112780 A1 | 5/2005 | Song | |
| 2006/0240541 A1 | 10/2006 | Petruno et al. | |
| 2007/0048807 A1 | 3/2007 | Song | |
| 2007/0134811 A1* | 6/2007 | Takeuchi et al. | 436/514 |
| 2010/0167264 A1* | 7/2010 | Lee | 435/5 |

FOREIGN PATENT DOCUMENTS

| | | |
|---|---|---|
| JP | 2001033454 | 2/2001 |
| JP | 2001133455 | 5/2001 |
| WO | 9706439 | 2/1997 |
| WO | 9709620 | 3/1997 |
| WO | WO 03/012389 A2 * | 2/2003 |
| WO | 2006106084 | 10/2006 |
| WO | 2007042219 | 4/2007 |
| WO | 2008105814 | 9/2008 |

* cited by examiner

TEST ELEMENT HAVING COMBINED CONTROL AND CALIBRATION ZONE

CROSS REFERENCE TO RELATED APPLICATION

This application is a U.S. National Phase of PCT/EP2009/008571, filed Dec. 2, 2009, which claims priority to European patent application serial number 08020964.6, filed Dec. 3, 2008. PCT/EP2009/008571 is incorporated herein by reference in its entirety.

FIELD OF THE INVENTION

The present invention concerns the technical field of test elements for the analysis of liquid sample materials or of sample materials which can be converted into a liquid form.

BACKGROUND OF THE INVENTION

Test elements which have one or more discrete zones containing immobilized reactants are frequently used to detect analytes in a sample or in a sample material. These zone are referred to in the following as analyte detection zones or detection zones. The analyte is bound in a reaction (assay) from the sample in the analyte detection zone by means of a specific interaction with the reactant. The binding events can be detected by measuring instruments e.g. by the optical detection of fluorescence signals. The test elements can be prepared with microarray structures and be present in the form of a biochip for the site-selective detection of binding reactions as described for example in the published applications WO 2007/042219 and EP1412533. The test elements can also be test strips on which for example one or more detection zones containing immobilized reactants are arranged in the form of strips or lines perpendicular to the flow direction of the sample. Such test strips are for example described in WO 2008/105814 and US 2004-0126767.

Labelled binding partners are used to detect the binding events between the reactants and the analyte in the analyte detection zone. These are reactants which comprise a labelling reagent and which interact specifically with the analyte. Fluorophores which emit a light signal after excitation by electromagnetic radiation of a certain wavelength can for example be used as labelling reagents. The measurability of this light signal in the analyte detection zone and its intensity indicate the presence of the analyte in the sample or are a measure for its concentration.

In the case of immunological detection methods the binding events on the test element are based on a specific antigen-antibody interaction (immunoassay). In immunological detection methods according to the sandwich principle the sample to be analyzed is typically brought into contact with a conjugate consisting of a labelling reagent and an analyte-specific binding partner (e.g. an antibody) so that complexes are formed between the analyte—if present in the sample—and the labelled conjugate. These complexes react with the immobilized reactants (e.g. antibodies) on the test element so that sandwich complexes consisting of the analyte-conjugate and the immobilized reactants which can be detected by means of the label, are present in the analyte detection zone. Examples of such immunoassays are described in the U.S. Pat. No. 4,168,146 (Grubb et al.) and U.S. Pat. No. 4,366,241 (Tom et. al.). A competitive assay is an alternative technique. In a competitive assay the labelling reagent is generally conjugated with a binding partner which is identical to the analyte or it is an analyte analogue. In this manner the labelled conjugate competes with the actual analyte for binding to the reactants in the analyte detection zone on the test element. A competitive assay is usually used to detect an antigen if only a single specific antibody is available for this antigen or if the antigen does not have sufficient binding sites for the unhindered binding of two antibodies. Hence, this assay variant is also suitable for detecting haptens. Examples of competitive assays are described in the U.S. Pat. No. 4,235,601 (Deutsch et. al.), U.S. Pat. No. 4,442,204 (Greenquist, et. al.) and U.S. Pat. No. 5,028,535 (Buechler et. al.).

Test elements in the form of immunological test strips are widely used devices for the rapid determination of drugs, pregnancy hormones, infectious diseases or so-called cardiac markers such as troponin T. In this connection qualitative tests which are merely read-out visually and often only give a "yes-no" answer and quantitative tests which are evaluated by means of a readout device are widely used.

Rapid tests for immunologically detectable substances have been known for a long time for a large number of different parameters, for example from WO 97/06439, EP 0 291 194, U.S. Pat. No. 5,591,645, U.S. Pat. No. 4,861,711, U.S. Pat. No. 5,141,850, U.S. Pat. No. 6,506,612, U.S. Pat. No. 5,458,852, U.S. Pat. No. 5,073,484. In these cases the immunological detection reagents (essentially labelled and unlabelled antibodies or antigens) are usually provided in a dry form on a support which allows the transport of a sample liquid (in particular body fluids such as blood, serum, plasma, urine, saliva etc.) on or in the support. For this purpose the support is preferably capillary-active and is for example a membrane or a plastic support provided with capillary channels (such as e.g. in U.S. Pat. No. 5,458,852). Among experts one often speaks about immunological or immunochromatographic test strips or test devices. These terms as well as the term "carrier-bound immunological test" or "carrier-bound immunological test elements" are often used synonymously and should also be used interchangeably in the following.

In addition to one or more analyte detection zones for the detection of one or more analytes, the test elements usually have a further zone in which the reactants are present which specifically bind the labelled binding partner. This zone is referred to as a control zone or indicator zone and serves as a function check for the labelled binding partner by capturing the labelled binding partner without requiring a direct involvement of the analyte. Analyte detection zone(s) and the control zone are usually spatially narrowly limited and arranged clearly separated from one another on the test element. In test elements in the form of a test strip in which the sample is applied in a liquid form and reaches the various zones with the aid of capillary forces, the control zone in the form of a control line is usually downstream of the analyte detection zone on or in the material through which a flow is possible. On such test strips the control zone additionally serves as a run check in order to ensure that the labelled binding partner has also actually reached the individual zones. The function of the control zone as a check for the functionality of the labelled binding partner and as a run check for the functionality of a test strip is also referred to by a person skilled in the art as "control function".

A test element is described in US 2007/0048807 A1 which has an indicator zone in addition to the detection zone on a porous membrane. A material (receptive material) is immobilized in the indicator zone which specifically binds with binding partners conjugated with labelling reagent which are not complexed with the analyte in the analyte detection zone.

Due to the spatial separation of the analyte detection zone and control zone, spatially resolving optical systems such as camera chips or two-dimensional or three-dimensional photodiode arrays for the analysis of the analyte detection zone and control zone are often present in the measuring device for evaluating the test elements. The signals of the optical systems are then converted by an appropriate evaluation software into concentration values and displayed.

If the labelling reagent of the labelled binding partner is a fluorophore, then in addition to checking the function of the labelled binding partner by means of a control zone, it is also necessary to calibrate the analyte-specific measurement signal. The analyte-specific measurement signal is the signal which can be generated in the analyte detection zone due to the presence of the analyte in the sample. The intensity of this signal depends on the irradiated energy in the excitation spectrum of the fluorophore which is localized by the analyte-specific interaction in the analyte detection zone. Experience shows that the energy generated by the radiation source is in turn subject to variations which, on the one hand, can be attributed to production-related variations between different radiation sources of the same type or, on the other hand, arise over the cycle of use of a radiation source. Such variations have to be corrected for a reproducible and reliable quantitative determination of the analyte. This is usually carried out by calibrating the analyte-specific measurement signal with a signal that has been generated by a standardized amount of the fluorophore. The standardized amount of the fluorophore is also referred to by a person skilled in the art as a fluorophore standard or calibration standard. The radiation emitted by the fluorophore standard after excitation with electromagnetic radiation is usually referred to as the "calibration signal".

In the systems used in the prior art for the (semi)quantitative determination of analytes, the analyte-specific measurement signal can be calibrated by generating the calibration signal outside the test element (for example TRIAGE® system, Biosite Inc.).

In addition there are systems in which the calibration of the analyte-specific measurement signal can be carried out directly with the test element. Such test elements comprise, in addition to the analyte detection zone and optionally the control zone, a further discrete zone spatially separated from the other zones in which the fluorophore as a labelling reagent is disposed in a defined amount directly on the test element. This zone is referred to in the following as a calibration zone. The presence of the calibration zone on the test element enables the calibration signal to be detected directly on the test element using the same measuring device or analyzer that also detects the signals of the analyte detection zone(s) and/or the control zone. In the case of a test strip or microarray, the signal detection can be carried out using the same spatially resolving optical system as the function check and measurement of the analyte-dependent signal in the analyte detection zone. In immunological test strips the calibration zone can for example be present in the form of a further line perpendicular to the flow direction of the sample (for example CARDIAC READER®, Roche Diagnostics).

The presence of a calibration zone on the test strip has the advantage that the stability requirement for the fluorophore in this zone is reduced to the life time of the test element lot. In contrast, if the calibration signal were to be generated outside the test element, the user would not only have to take care that the test strip is adequately stable but also that the separately used fluorophore standard is stable enough, whereby an additional source of error has to be avoided in each case. Since the generation and detection of the calibration signal outside the test element usually requires additional radiation sources, filters etc. and a separate optical evaluation system, the corresponding analyzers have a more complex construction, are larger and usually also more expensive.

The term "calibration function" is also commonly used in connection with the phrase "calibration of the analyte-specific measurement signal". The term "calibration function" is known to a person skilled in the art just like the phrase "calibration of the analyte-specific measurement signal" and relates to means that are used to generate the calibration signal within an analyzer for example on a test carrier or, as described above, outside a test carrier.

A test element can also be used to determine several different analytes simultaneously in a sample. In the case of such "panel tests" a discrete detection zone containing analyte-specific reactants is present for each analyte on the test element. Since one analyzer is usually used to evaluate different test elements for determining different medical parameters in the laboratory or by practicing doctors, the corresponding test elements must have a uniform size which is standardized with respect to the instrument. For this reason, less and less space is available for the control and calibration zone as the number of analyte detection zones on the test element increases. Moreover, the size of the test element itself is limited by the requirement of an adequate wetting of the test area by the usually small sample volumes. Since in addition there must be a spatial separation between the calibration and analyte detection zone, the number of analyte detection zones on the test element is limited and thus also the number of analytes that can be detected using one test element. In order to nevertheless detect as many analytes as possible with the aid of a test carrier for a panel test, it is therefore often necessary to carry out the measurements required to calibrate the analyte-specific measurement signal outside of the test element. However, this requires correspondingly complicated adaptations of the analyzer or measuring instrument and/or the use of additional test elements and, for the above-mentioned reasons, also requires more time and effort by the laboratory staff.

It is against the above background that the present invention provides certain unobvious advantages and advancements over the prior art. In particular, the inventor has recognized a need for improvements in a test element having a combined control and calibration zone.

SUMMARY OF THE INVENTION

Although the present invention is not limited to specific advantages or functionality, it is noted that the present invention provides a test element for conducting specific binding assay.

In accordance with one embodiment of the present invention, the element includes analyte detection zone and a combined control and calibration zone. The combined control and calibration zone includes a fluorophore and a binding partner for the specific binding of a reagent labelled with a fluorophore. In one particular example, the test element can be used in an immunological sandwich assay.

In other embodiments, the fluorophore and the binding partner for the specific binding of a reagent labelled with a fluorophore are immobilized in the combined control and calibration zone. The fluorophore in the combined control and calibration zone and the fluorophore of the reagent labelled with a fluorophore may be excited at the same wavelength and emit electromagnetic radiation of the same wavelength. The test element can be an immunological chromatographic test strip or a microarray.

In a further embodiment, the invention is directed to a method for calibrating an analyte-specific measurement with the test element of claim and an analyzer suitable for evaluating the test element. The method includes:

a) generating a signal in the combined control and calibration zone by exciting the fluorophore in the combined control and calibration zone in the absence of the reagent labelled with a fluorophore,
b) measuring the signal generated in step a),
c) contacting the sample with the test element and with the reagent labelled with a fluorophore so that the analyte, if present in the sample, results in a detectable signal in the analyte detection zone;
d) generating a signal in the analyte detection zone by exciting the fluorophore of the reagent labelled with a fluorophore present in the analyte detection zone in the presence of the analyte,
e) measuring the signal generated in step d),
f) relating the signals measured in steps b) and e).

The method may further include:
g) comparing the relationship from step f) with a calibration curve,
h) determining the concentration of the analyte on the basis of the comparison carried out in step g).

In the various methods of the invention, the signals measured in steps b) and e) may be offset against one another. In addition, the generation of a signal in the combined control and calibration zone by excitation of the fluorophore in the combined control and calibration zone in the absence of the reagent labelled with a fluorophore (step a)) and the measurement of the signal generated by the fluorophore (step b)) may take place before the sample has been contacted with the test element and with the reagent labelled with a fluorophore (step c)).

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE FIGURES

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DESCRIPTION

The subject matter of the invention is a test element, for example, in the form of an immunological test strip functioning according to the sandwich principle, for the fluorophoric detection of one or more analytes in a sample comprising an analyte detection zone and a combined control and calibration zone, wherein the combined control and calibration zone comprises a fluorophore and binding partners for the specific binding of reagents labelled with a fluorophore.

Furthermore, the invention concerns a method for calibrating an analyte-specific measurement signal, a method for determining the concentration of an analyte in a sample and the use of the test element for calibrating a signal generated in the analyte detection zone of a test element.

The object of the present invention is to eliminate the disadvantages of the prior art. In particular it is an object of the present invention to provide a test element in which the calibration of the analyte-specific measurement signal can be carried out directly with the test element and to arrange the control and calibration zones on the test element in such a manner that it is also possible to detect a large number of analytes with the aid of the test element.

In test elements in which the specific detection of one or more analytes in a sample takes place with the aid of fluorophores, the invention enables the detection of the signal for the control function and the signal for the calibration function in one discrete, spatially delimited zone. According to the invention it is proposed that an additional zone is arranged in a test element in addition to the usual analyte detection zone. This zone which in the following is referred to as a combined control and calibration zone, is present in the test element spatially separated from the analyte detection zone and it comprises a fluorophore as well as binding partners for the specific binding of reagents labelled with a fluorophore. The spatial separation of the combined control and calibration zone and analyte detection zone takes place in such a manner that the analyte detection zone and combined control and calibration zone are each present as discrete, spatially delimited zones.

Hence, the present invention concerns a test element for the fluorophoric detection of one or more analytes in a sample comprising
 an analyte detection zone and
 a combined control and calibration zone,
 characterized in that the combined control and calibration zone comprises
 a) fluorophore and
 b) binding partners for the specific binding of reagents labelled with a fluorophore.

Suitable fluorophores are known to a person skilled in the art. In a preferred embodiment the fluorophore of the fluorophore in the combined control and calibration zone and/or the fluorophore of the reagents labelled with the fluorophore is a fluorescent dye or a fluorescent label. The terms fluorescent dye, fluorescent label or fluorescent marker are used synonymously in the following. Typical fluorescent labels that are suitable for the invention can for example be fluorescent proteins (such as GFP and its derivatives), Cy3, Cy5, Texas Red, fluorescein and the Alexa dyes (e.g. Alexa 568). Further fluorescent labels can for example be obtained from the Invitrogen Company.

The reagents labelled with the fluorophore are a binding partner which is labelled with the fluorophore such that the binding partner can be detected by means of the label. The reagents labelled with the fluorophore are able to specifically interact with the analyte. This interaction can be in the form of a direct or indirect binding. It is important that the analyte can be detected by means of the label as a result of the specific interaction of the fluorophore-labelled reagents with the analyte.

The number of analyte detection zones on a test element is limited by the area of the test element which is limited by the requirement to adequately wet the test area by the usually small sample volumes and by the necessity to spatially separate the calibration, control and analyte detection zone(s). The combined control and calibration zone according to the invention allows at least one additional analyte detection zone on the test element without the user having to use an additional test element or revert to a correspondingly more complicated analytical system which allows the analyte-specific measurement signal to be calibrated only with the aid of a fluorophore standard outside of the test element.

In one embodiment of the invention the test element is a biochip in which the analyte detection zone(s) and the combined control and calibration zone are arranged in the form of a microarray. Such arrays which include "gene chips", "protein chips", "antibody arrays" or such like are known to a person skilled in the art and are usually manufactured from polycations, nitrocellulose or biotin-coated glass carriers, cover slips or from membranes such as nitrocellulose or nylon membranes.

In a preferred embodiment the test element is a test strip in which the analyte detection zone and the combined control and calibration zone are arranged such that liquid can be transported between the zones. For this purpose the test strip typically usually contains a permeable material (e.g. paper, fleece, membrane, capillary channel) which is optionally fastened to an inert carrier.

Each test element typically has one or more sample application zones, suction zones, chromatographic zones, detection zones, reaction zones, control zones and/or calibration zones. It is only important for the invention that at least one (analyte) detection zone and at least one combined control and calibration zone is present.

In one embodiment of the invention the analyte detection zone and/or the combined control and calibration zone are present in the form of a line or an essentially round spot.

All test elements are suitable as a test element in the sense of the invention which are based on specific binding reactions and in which the specific binding reaction is detected with the aid of a signal generated by a fluorophore. Appropriate specific binding reactions are known to a person skilled in the art. Examples of these are the binding pairs:
 antibody with hapten, antigen or other antibodies (for example species-specific antibody-antibody interactions) where in some cases fragments of these species may be sufficient;
 biotin with avidin or streptavidin;
 hormone with hormone receptor;
 sugar with lectin;
 nucleic acid with complementary nucleic acid and such like.

In a particularly preferred embodiment the test element is a test element in the form of an immunological test strip functioning according to the sandwich principle.

In order to achieve the object according to the invention it is irrelevant whether the fluorophore in the combined control and calibration zone and the fluorophore of the reagents labelled with the fluorophore emit at different wavelengths and/or in different spectral ranges. Thus, within the context of the invention it is also not necessary that the fluorophore in the combined control and calibration zone and the fluorophore of the reagents labelled with the fluorophore have an identical structure.

In a preferred embodiment of the invention the fluorophore in the combined control and calibration zone and the fluorophore of the reagents labelled with the fluorophore have the same structural element. Such structural elements that are characteristic for fluorophores are known to a person skilled in the art. In another preferred embodiment the fluorophore in the combined control and calibration zone and the fluorophore of the reagents labelled with the fluorophore are identical.

An embodiment of the present invention is particularly preferred in which the fluorophore in the combined control and calibration zone and the fluorophore of the reagents labelled with the fluorophore can be excited at essentially the same wavelength and, as a consequence of this excitation, emit electromagnetic radiation of essentially the same wavelength. The advantage of this embodiment is that in each case the same components (radiation source, wavelength, filters etc.) can be used for the excitation and detection of the emitted signal of the fluorophore in the combined control and calibration zone and the fluorophore of the reagents labelled with the fluorophore and thus complex constructional adaptations of the usually small and compact laboratory instruments are avoided.

The labelling of the reagents labelled with the fluorophore is carried out directly or indirectly by methods which are known to a person skilled in the art. In the case of direct labelling the fluorophore is coupled directly (covalently or non-covalently) to the binding partner. In the case of indirect labelling a secondary binding partner which carries the label (covalently or non-covalently) is for example bound to the analyte-specific binding partner. Suitable secondary or also tertiary binding partners can be antibodies, secondary antibodies or the known streptavidin/biotin system.

The fluorophore and the binding partners for the specific binding of reagents labelled with a fluorophore must be present in the combined control and calibration zone in such a manner that two requirements are fulfilled:
 1. In the absence of the reagents labelled with a fluorophore, it is possible to generate a detectable signal by specific excitation of the fluorophore in the combined control and calibration zone, and
 2. the presence of the reagents labelled with the fluorophore in the combined control and calibration zone enables a detectable signal which is a measure for the presence of the reagents labelled with a fluorophore in the zone.

In order to fulfil these requirements, the fluorophore and the binding partners for the specific binding of the reagents labelled with a fluorophore are used in the combined control and calibration zone in a certain concentration and amount within a certain tolerance range. The tolerance range must be selected such that the control as well as the calibration function can be utilized and the signal of the calibration function i.e. the signal generated by the fluorophore in the combined control and calibration zone has no effect on the intensity of the signal of the control function i.e. of the signal of the reagents labelled with a fluorophore.

In the combined control and calibration zone of the test element according to the invention the amount of fluorophore is preferably between 0.001 μg and 5 μg, whereas the amount of binding partners for the specific binding of the reagents labelled with a fluorophore is between 1 ng and 500 ng. In the combined control and calibration zone an amount of fluorophore between 0.1 μg and 1 μg is particularly preferred and an amount of binding partners for the specific binding of the reagents labelled with a fluorophore is particularly preferably between 10 ng and 50 ng.

A preferred embodiment of a test element according to the invention comprises a combined control and calibration zone which has been produced by impregnation of the test element, characterized in that a fluorophore in a solution at a concentration between 0.25 nmol/ml and 2.5 nmol/ml and the reagents labelled with a fluorophore in a solution at a concentration between 0.01 mg/ml and 5 mg/ml were used for the impregnation. In a particularly preferred embodiment of the test element the combined control and calibration zone was produced by impregnating the test element with the dissolved fluorophore at a concentration between 1 nmol/ml and 2 nmol/ml and with the dissolved reagents labelled with a fluorophore at a concentration between 0.1 mg/ml and 1 mg/ml.

Impregnation is a standard method for applying the components required for the test to test elements for example in the form of a line on an immunological test strip. The amount of the components in solution that has to be used for the impregnation depends on the material of the respective test element and is known to a person skilled in the art.

In a preferred embodiment the amount and concentration of the fluorophore and of the binding partners for the specific binding of the reagents labelled with a fluorophore in the combined control and calibration zone is selected such that the signal of the control function is stronger than the signal of the calibration function. This means that the amount or concentration of the fluorophore and of the binding partners for the specific binding of the reagents labelled with a fluorophore in the combined control and calibration zone of the test element according to the invention is selected such that the number of fluorophores is smaller than the number of reagents labelled with a fluorophore after binding to the binding partners for the specific binding of the reagents labelled with a fluorophore.

A person skilled in the art is able to determine these values for the respective fluorophores and for the binding partners for the specific binding of the reagents labelled with a fluorophore and to define the corresponding tolerance range which can usually have certain variations with regard to the test carrier used and the fluorophore or fluorophores that are used.

In a preferred embodiment of the test element according to the invention the binding partners for the specific binding of reagents labelled with a fluorophore and/or the fluorophore in the combined control and calibration zone are immobilized. The immobilization can be carried out in a type and manner known to a person skilled in the art. The immobilization can be based on covalent bonds or on non-covalent interactions such as those that are for example characteristic for the streptavidin/biotin interaction system.

The fluorophore and the binding partners for the specific binding of reagents labelled with a fluorophore can be present in the combined control and calibration zone directly immobilized on the test element or be indirectly immobilized by binding to suitable carrier molecules or binding structures in the test element. The carrier molecules can for example be specific binding partners for the fluorophore and/or for the binding partners for the specific binding of reagents labelled with a fluorophore so that the immobilization occurs non-covalently as a result of the specific interaction with the carrier molecule. The carrier molecule itself can in turn be directly or indirectly immobilized on the test element by means of further binding partners/carrier molecules or suitable binding structures.

It is unimportant for the invention whether the localization of the fluorophore and/or the binding partners for the specific binding of reagents labelled with a fluorophore already takes place in the combined control and calibration zone when the test element is produced, or not until shortly before the calibration of the measurement signal for example in that the fluorophore and/or the binding partners for the specific binding of reagents labelled with a fluorophore are previously brought into contact in a dissolved form in a suitable solvent with the test element under conditions that enable an immobilization in the combined control and calibration zone.

Analytes suitable for the invention are analytes which can be detected on the basis of a specific binding pair relationship. For the preferred case of a test element in the form of an immunological test strip that functions according to the sandwich principle these are in particular antibodies, antigens, haptens (in each case including fragments thereof). The following immunologically detectable analytes are particularly preferred: hCG, BNP, (NT-)proBNP, troponin I, troponin T, myoglobin, D-dimer, CRP, HIV, HCV, CD40, CK-MB, TSH etc.

All liquid sample materials or sample materials that can be converted into a liquid form are suitable according to the invention as a sample from which the analytes can be determined. In particular body fluids such as blood and fractions derived therefrom (serum, plasma), saliva, urine, cerebrospinal liquid, sperm, interstitial fluid, sweat and such like are suitable. Sample materials that are per se not liquid but can be transferred into the liquid phase by solution or suspension in solvents and in particular in aqueous solvents are also suitable.

Reactants contained in the test element or which are to be added to the test element or to the sample (also referred to synonymously as "binding partners" or "specific binding partners") undergo a selective (binding) reaction with the analyte or, in the case of binding partners for the specific binding of reagents labelled with a fluorophore, with the reagents labelled with a fluorophore. They enable a direct or indirect inference to be made about the amount of analyte present in the sample.

Preferred binding partners are antibodies (AB), in particular polyclonal antibodies (PAB) or monoclonal antibodies (MAB) as well as antigens and haptens as well as fragments thereof provided they are active for the purposes of the specific analyte detection.

Some of the reactants or reagents are preferably provided on the test element in such a manner that they can be detached therefrom by the sample liquid, for example by impregnating suitable carrier materials such as fleeces, membranes etc. or by applying and drying them in appropriate (capillary) channel structures.

It is, however, also possible to add at least one reactant or one of the reagents in a dissolved form to the test element for example by adding the solution to the sample or applying the solution to the test element independently of the sample. According to the invention it is also possible although less preferred to use all specific reactants and/or reagents in a solution or in several solutions for the analysis. Then on the test element there is only one further reactant in the analyte detection zone which, as a binding partner, can capture a reactant that is specifically bound to the analyte as the specific binding partner and which is not the reagent labelled with the fluorophore and thus result in an indirect binding of the analyte in the analyte detection zone of the test element. Similarly there is a binding partner in the control zone which can capture the reagent labelled with the fluorophore without requiring a direct involvement of the analyte.

The binding partner for the specific binding of the reagents labelled with a fluorophore that is preferably immobilized in the combined control and calibration zone is able to specifically bind the reagents labelled with a fluorophore. The binding partner can for example be an analyte analogue or, in the case of a competitive test procedure, be an antibody which is directed against certain epitopes on the reagents labelled with a fluorophore which are not analyte-specific. It is important that the binding partner for the specific binding of the reagents labelled with a fluorophore can capture the reagents labelled with a fluorophore in the combined control and calibration zone without requiring a direct involvement of the analyte.

The invention also concerns a method for calibrating an analyte-specific measurement signal using the test element according to the invention and an analyzer suitable for evaluating the test element according to the invention, comprising the following steps:
  a) generating a signal in the combined control and calibration zone by exciting the fluorophore in the combined control and calibration zone in the absence of the reagents labelled with a fluorophore,
  b) measuring the signal generated in step a) in the combined control and calibration zone,
  c) contacting the sample with the test element and with the reagents labelled with a fluorophore so that the analyte, if present in the sample, results in a detectable signal in the analyte detection zone;
  d) generating a signal in the analyte detection zone by exciting the fluorophore of the reagents labelled with a fluorophore which are present in the analyte detection zone in the presence of the analyte,
  e) measuring the signal generated in step d) in the analyte detection zone,
  f) relating the signals measured in steps b) and e).

For the method according to the invention a suitable analyzer for evaluating the test element is provided in addition to the test element according to the invention. Suitable devices and analyzers for this are known to a person skilled in the art from the prior art. They for example include imaging/scanning detection systems which enable the measurement or evaluation of analyte-specific signals from the analyte detection zone and signals from the control and calibration zone in one instrument. However, it is important according to the invention that the signal generated by the fluorophores in the analyte detection zone as well as the signal generated by the fluorophores in the combined control and calibration zone are detected by the analyzer. The TRIAGE® analyzer from the Biosite Company is mentioned as a typical analyzer or measuring device.

The signals generated in the method according to the invention are electromagnetic radiation that is emitted after excitation of the fluorophore. The excitation usually takes place by specifically irradiating the fluorophore with electromagnetic radiation of an (excitation) wavelength that is characteristic for the particular fluorophore. It is irrelevant whether excitation takes place with electromagnetic radiation of a wavelength corresponding to the maximum excitation or with electromagnetic radiation of another wavelength provided the irradiation leads to the emission of a detectable signal whose intensity is a measure for the amount of the excited fluorophore.

The sample is brought into contact with the test element and with reagents that are specific for the analyte and the analyte, if present in the sample, leads to a detectable signal in the analyte detection zone by interacting with the specific reagents, the signal being due to the reagents labelled with a fluorophore. It is important that the intensity of the measurement signal depends on the amount of analyte in the sample.

In order to calibrate the analyte-specific measurement signal, the signals measured in the combined control and calibration zone and in the analyte detection zone (steps b) and e) of the method according to the invention) must be related to one another. In this connection the signal measured in step b) in the combined control and calibration zone serves as a reference for the actual analyte-dependent signal which is generated in the analyte detection zone. In a preferred embodiment of the method according to the invention the signals measured in the combined control and calibration zone and in the analyte detection zone are offset against one another. In a particularly preferred embodiment of the method according to the invention these two signals are offset according to the following formula:

$$\text{signal(calibrated)} = \text{signal(analyte detection zone)}/\text{signal(control and calibration zone)}.$$

In this case "signal (analyte detection zone)" corresponds to the signal measured in step d) of the method according to the invention and "signal (control and calibration zone)" corresponds to the signal measured in step b) of the method according to the invention.

The offsetting of the signals detected in steps b) and e) of the method according to the invention from the analyte detection zone and the combined control and calibration zone can for example take place in a central computer unit of the analyzer.

The result of the offsetting of the signals detected in steps b) and e) of the method according to the invention from the analyte detection zone and the combined control and calibration zone can for example be compared with a calibration curve in order to determine the analyte concentration. Thus, the invention also comprises a method for determining the concentration of an analyte in a sample using the test element according to the invention and a suitable analyzer for evaluating the test element according to the invention comprising the following steps:
  a) generating a signal in the combined control and calibration zone by exciting the fluorophore in the combined control and calibration zone in the absence of reagents labelled with a fluorophore,
  b) measuring the signal generated in step a) in the combined control and calibration zone,
  c) contacting the sample with the test element and with the reagents labelled with a fluorophore so that the analyte, if present in the sample, leads to a detectable signal in the analyte detection zone,
  d) generating a signal in the analyte detection zone by exciting the fluorophore of the reagents labelled with a fluorophore that are present in the analyte detection zone in the presence of the analyte,
  e) measuring the signal generated in step d) in the analyte detection zone,
  f) relating the signals measured in steps b) and e)
  g) comparing the relationship from step f) with a calibration curve,
  h) determining the concentration of the analyte on the basis of the comparison carried out in step g).

The calibration curve used in the method according to the invention is obtained by measuring standard solutions containing known amounts of analyte; preferably in this process the analyte-specific measurement signal is calibrated in each case according to the method according to the invention for calibrating analyte-specific measurement signals.

For the method according to the invention it is irrelevant whether the generation and measurement of the signal in the combined control and calibration zone by excitation of the fluorophore in the combined control and calibration zone (steps a) and b) of the method according to the invention) takes place before or after contacting the sample with the test element. It is important that the signal generated by excitation of the fluorophore immobilized in the combined control and calibration zone takes place in the absence of the reagents labelled with a fluorophore which can be specifically bound by the binding partners immobilized in the combined control and calibration zone.

One embodiment of the method according to the invention is characterized in that the generation of the signal in the combined control and calibration zone by excitation of the fluorophore in the combined control and calibration zone in the absence of the reagents labelled with a fluorophore (step a)) and the measurement of the signal generated by the fluorophore (step b)) take place after the sample has been contacted with the test element and with the reagents labelled with a fluorophore (step c)). Thus, for example the sample could be brought into contact with the test carrier and with the reagents labelled with a fluorophore before placing the test carrier in the analyzer. Then the calibration signal is generated and measured before the reagents labelled with a fluorophore have reached the combined control and calibration zone on the test carrier for example with the aid of capillary forces. The sample can also be brought into contact with the test carrier before generating and measuring the calibration signal without the sample having to come into contact with the reagents labelled with a fluorophore for example because the reagents labelled with a fluorophore are not present on the test carrier and are not brought into contact with the sample until after detection of the calibration signal.

It is also possible that the sample is firstly brought into contact with the test element and the measurement of the signal takes place in the analyte detection zone (corresponding to step e) of the method according to the invention). If the reagents labelled with a fluorophore have then reached the combined control and calibration zone on the test carrier for example with the aid of capillary forces, the reagents labelled with a fluorophore that have been specifically bound by the binding partners immobilized in the combined control and calibration zone, must be removed from the test carrier for example by one or more washing steps. Only then should the calibration signal that is additionally required for calibrating the analyte-specific measurement signal be generated and measured in the combined control and calibration zone (corresponding to steps a) and b) of the method according to the invention).

In a preferred embodiment of the method according to the invention the signal in the combined control and calibration zone is generated by exciting the fluorophore in the combined control and calibration zone in the absence of reagents labelled with a fluorophore (step a)) and the signal generated by the fluorophore is measured (step b)) before the sample is brought into contact with the test element and with the reagents labelled with a fluorophore (step c)).

The invention also concerns the use of the test element according to the invention to calibrate a signal generated in the analyte detection zone of a test element. In one embodiment of the use according to the invention the analyte-specific signals are generated with the aid of another test element.

Figure 1:
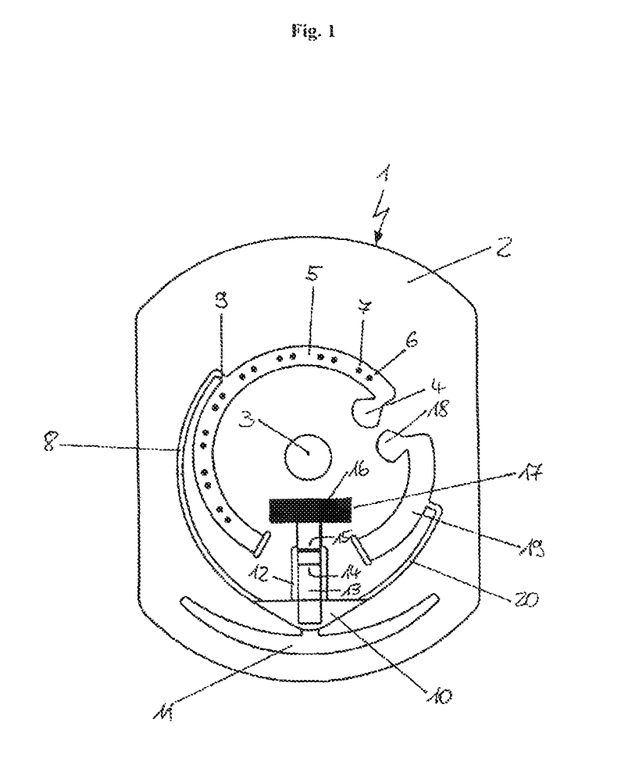
FIG. 1 shows a schematic diagram of a top-view of one embodiment of the test element (1) according to the invention having an analyte detection zone (14) and a combined control and calibration zone (15).

FIG. 1 shows a schematic diagram of a top-view of one embodiment of the test element (1) according to the invention having an analyte detection zone (14) and a combined control and calibration zone (15).

Figure 2:
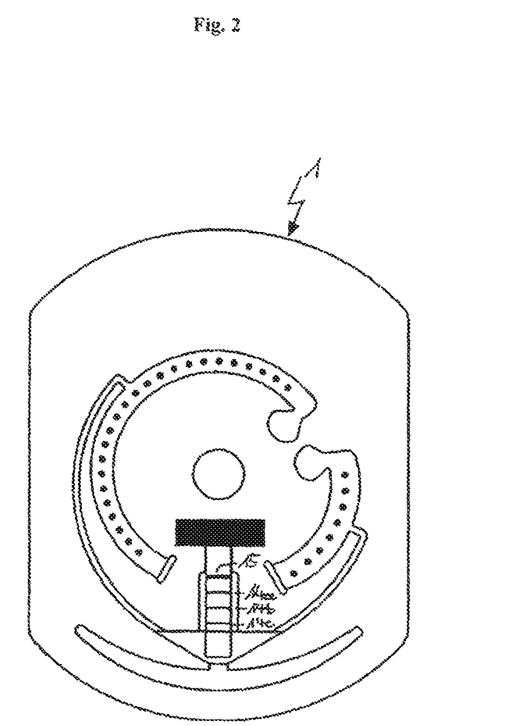
FIG. 2 shows a schematic diagram of a top-view of one embodiment of the test element (1) according to the invention having several analyte detection zones (14a), (14b), (14c) ("panel test") and a combined control and calibration zone (15).

FIG. 2 shows a schematic diagram of a top-view of one embodiment of the test element (1) according to the invention having several analyte detection zones (14a), (14b), (14c) ("panel test") and a combined control and calibration zone (15).

Figure 3A:
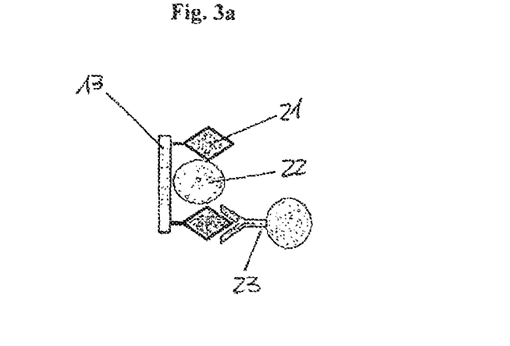
FIG. 3a shows a schematic diagram of an embodiment of the combined control and calibration zone on a porous matrix (13).

FIG. 3a shows a schematic diagram of an embodiment of the combined control and calibration zone on a porous matrix (13) containing immobilized g-globulin-JG9 latex (22) as a fluorophore and immobilized troponin T polyhapten (21) as the binding partner for the specific binding of reagents labelled with a fluorophore, wherein a conjugate consisting of a latex JG9 fluorophore and a troponin T-specific monoclonal antibody (MAB<TnT>Lx) (23) is bound as a reagent labelled with a fluorophore to an immobilized troponin T polyhapten (21). JG9 is a squaric acid derivative.

Figure 3B:
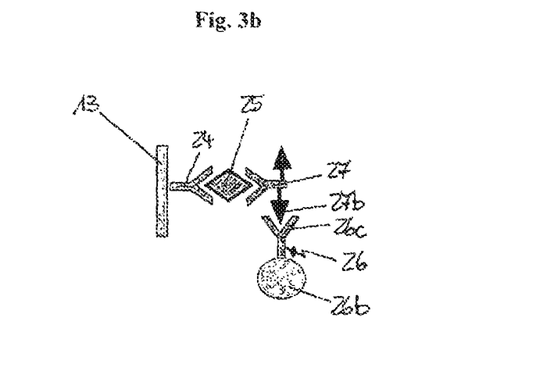
FIG. 3b shows a schematic diagram of an embodiment of an analyte detection zone in which the analyte-specific reactants are directly immobilized on the test element.

FIG. 3b shows a schematic diagram of an embodiment of an analyte detection zone in which the analyte-specific reactants are directly immobilized on the test element. The analyte detection zone consists of a troponin T-specific monoclonal antibody (MAB<TnT>) (24) which is immobilized as an analyte-specific reactant directly on the porous matrix (13) of the test element. Troponin T (25) as the analyte is present in a sandwich complex with the immobilized MAB<TnT> (24) and with a reagent labelled with a fluorophore (26), wherein JG9-Lx (26b) as a fluorophore indirectly labels the analyte via a further analyte-specific binding partner (27). The analyte-specific binding partner (27) is a conjugate containing digoxigenin (27b) and the indirect labelling with the reagent labelled with a fluorophore is mediated by the specific interaction of the anti-digoxin binding partner (26c) with the digoxigenin (27b) of the analyte-specific binding partner (27).

Figure 3C:
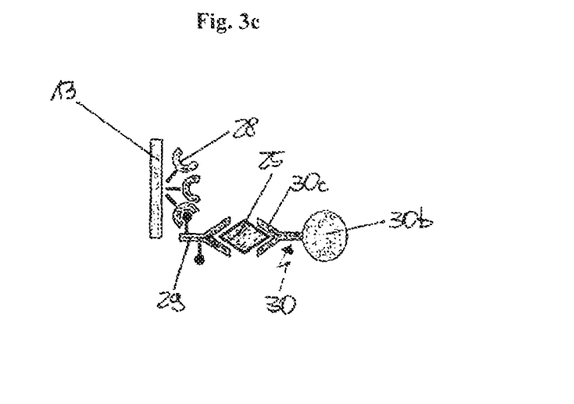
FIG. 3c shows a schematic diagram of an embodiment of an analyte detection zone in which the analyte-specific reactants are indirectly immobilized on a test element.

FIG. 3c shows a schematic diagram of an embodiment of an analyte detection zone in which the analyte-specific reactants are indirectly immobilized on a test element. The analyte detection zone consists of streptavidin molecules (28) which are directly immobilized on the porous matrix (13) of a test element. A sandwich complex consisting of a biotinylated troponin T-specific monoclonal antibody (MAB<TnT>-Bi) (29), troponin T (25) and a conjugate of a latex JG9 fluorophore and a troponin T-specific monoclonal antibody (MAB>TnT>-Lx) (30) is bound to the streptavidin molecules (28). The biotinylated troponin T-specific monoclonal antibody (MAB<TnT>-Bi) (29) is the analyte-specific reactant, troponin T (25) is the analyte and the conjugate (30) consisting of a latex-JG9 fluorophore (30b) and a troponin T-specific monoclonal antibody (MAB<TnT>-Lx) (30c) represents the reagent labelled with a fluorophore.

Example 1

Preparation of a Test Element for Detecting Troponin T

The test element (1) comprises a substrate (2) which contains the fluidic and microfluidic as well as chromatographic structures. The substrate (2) is covered by a corresponding counterpiece (cover layer) (not shown in FIG. 1) which contains sample application and vent openings which correspond to the structures in the substrate (2). The substrate is manufactured by injection moulding from polycarbonate (PC) (cyclo olefin copolymers (COC), polystyrene (PS), ABS plastic or polymethyl methacrylate (PMMA) are also possible as alternative materials) (dimensions about 60×80 mm$^2$). The surface of the substrate (2) which has the fluidic structures can be purified by plasma treatment and hydrophilized. The substrate surface can also be hydrophylized chemically by using detergents.

The cover layer as well as the substrate (2) have a central recess (3) which interacts with a corresponding drive unit in a measuring device to allow a rotation of the disk-shaped test element (1). The test element contains a sample application opening (4) by means of which sample and in particular whole blood is added to the test element. The sample application opening (4) is fluidically connected to a primary channel section (5) which contains the analyte-specific reactant (6) and the reagents (7) labelled with a fluorophore. The analyte-specific reactants (6) are in this case a biotinylated troponin T-specific monoclonal antibody (MAB<TnT>-Bi); the reagents (7) labelled with a fluorophore are conjugates of a latex JG9 fluorophore and a troponin T-specific monoclonal antibody (MAB<TnT>-Lx). JG9 is a squaric acid derivative.

The analyte-specific reactants (6) and the reagents (7) labelled with a fluorophore are alternately introduced as spot-shaped reagent spots into the primary channel section (5) by means of piezo dosing and subsequently dried so that almost the entire inner surface is covered with reagents.

The reagent solutions have the following composition:
Analyte-Specific Reactants:

| MES: | 50 mM, pH 5.6 |
|---|---|
| BPLA new: | 1% |
| Synperonic P85: | 0.2% |
| sucrose: | 4% |
| MAB 33: | 3 mg/ml |
| MAB 33/Fab'l-poly: | 2 mg/ml |
| MAB<TnT>M11.7-F(ab')2-Bi: | 100 µg/ml |

Reagents Labelled with a Fluorophore:

| HEPES: | 50 mM pH 7.4 |
|---|---|
| PAB<->B-IgG | 1% |
| Synperonic P85 | 0.15% |
| sucrose: | 4% |
| NaCl: | 200 mM |
| MAB33: | 3 mg/ml |
| MAB33/Fab'l-poly: | 2 mg/ml |
| MAB<TnT>M7-IgG-Lx (JG9): | 0.35% |

The primary channel section (5) is fluidically connected to a secondary channel section (8) via a capillary stop (9). The capillary stop (9) can be configured as a geometric valve or hydrophobic barrier so that the amount of sample flowing through the capillary stop (9) can be controlled by centrifugal forces by means of the speed of rotation of the test element (1). The plasma collection zone (10) and the erythrocyte collection zone (11) which are in the form of chambers adjoin the secondary channel section (8). The separation of red corpuscles or other cellular sample components is started in the secondary channel section (8) at suitable speeds of rotation. The reagents contained in the primary channel section (5) are already dissolved when sample liquid enters the secondary channel section (8). Components of the sample-reagent mixture are captured in both collection zones (10) (11). The plasma collection zone (10) is in fluidic connection with a measuring chamber (12) which contains a porous matrix (13).

The porous matrix (13) (nitrocellulose membrane on a plastic carrier foil; 21×5 mm$^2$; cellulose nitrate membrane strengthened with 100 µm PE foil (type CN 140 from Sartorius, Germany)) is introduced into a corresponding recess in the substrate and optionally fastened by means of a double-sided adhesive tape. An analyte detection zone (14) and a combined control and calibration zone (15) which have been generated by line impregnation before introducing the porous matrix are present on the porous matrix (13) each in the form of a line. In this connection the analyte detection zone (14) is applied to the previously described cellulose nitrate membrane by applying an aqueous streptavidin solution (4.75 mg/ml) by line dosing. The dosing is selected such that (dosing amount 0.12 ml/min, sheet speed 3 m/min) a line with a width of about 0.4 mm is formed. This line serves to detect the analyte to be determined and contains about 0.95 µg streptavidin per membrane. The combined control and calibration zone (15) is generated at a distance of about 4 mm downstream of the streptavidin line by applying an aqueous mixture of a troponin T polyhapten solution at a concentration of 0.1 mg/ml and of g-globulin JG9 latex at a concentration of 0.03% under identical dosing conditions. This combined control and calibration zone (15) contains about 0.02 µg polyhapten and 0.06 µg g-globulin JG9 latex per test.

After introducing the porous matrix (13) into the substrate (2) the cover (foil or injection moulded part without fluidic structures which can be optionally hydrophilized) is applied and optionally permanently connected to the substrate (2) and preferably glued, welded or clipped.

Finally the substrate is turned and placed in the corresponding recess of a waste fleece (16) (fleece 13×7×1.5 mm$^3$ in size) consisting of 100 parts glass fibre (diameter 0.49 to 0.58 µm, length 1000 µm) and 5 parts polyvinyl alcohol fibres (Kuralon VPB 105-2 from Kuraray) having a weight per unit area of about 180 g/ml$^2$) which is then fastened in the substrate (2) by means of an adhesive tape. Thus, the waste fleece (16) is present in a waste chamber (17) which is arranged behind the measuring chamber (12) in the flow direction. Reaction participants, sample and/or reagent components can be disposed of in the waste chamber (17) after they have flowed through the measuring chamber (12).

Furthermore, the test element can comprise an application opening for a washing solution (18) which is in fluidic connection with a washing solution channel (19) which in turn is fluidically connected via a washing solution feeding channel (20) to the measuring chamber (12). Washing solution can be led into the measuring chamber (12) to wash the porous matrix (13) with the aid of these structures and suitable centrifugation steps.

Example 2

Evaluation of a Test Element for Detecting Troponin T

Test elements from example 1 were used to detect troponin T in three different samples containing known troponin T concentrations. Two of the samples contained troponin T at a concentration of 0.1 ng/ml and 10 ng/ml in heparin whole blood. The samples were prepared by the usual dilution of a troponin T stock solution of 100 ng/ml which was previously prepared by dissolving the required amount of a troponin T lyophilisate from the Roche Company in a human serum. A third sample contained only heparin whole blood and served as a negative control. A different test element according to Example 1 was used for each sample.

The troponin T detection was carried out in each case under two different evaluation conditions. Both conditions differed technically in their radiation source as well as the properties of the filters for generating the excitation wavelength and the camera filter for measuring the emission wavelength for the fluorophore (JG9 latex) that was used. In one case it was a laboratory assembly with a 100 W halogen lamp; the filters covered a wide range not at the respective maximum of the fluorophore, the so-called "Redbox". In the other case it was a further developed assembly with a 100 W xenon lamp; the filters covered a narrower range nearer to the respective maximum of the fluorophore, the so-called "Linosbox 1". Both conditions differed greatly from the usual variations between different evaluation devices which have an effect on the strength of the respective analyte-dependent signal measured in the analyte detection zone and thus require a calibration of the measurement signal in order to obtain comparable results for the analyte determination on different instruments and should thus illustrate the effectiveness of the method. The "Linosbox" was used as the evaluation instrument itself.

Before the sample is applied for the actual troponin T test, the signal of the combined control and calibration zone on the test element was determined in each case in the Redbox and Linosbox 1 after excitation with radiation of an excitation wavelength of 633 nm ("dry measurement", see Table 1). Although the absolute signal strengths differed between the Redbox and Linosbox 1 in their absolute values, there was on average as expected no significant variation between the individual samples (see Table 1, line "mean").

TABLE 1

Determination of the signal in the analyte detection zone before application of the sample to the test element ("dry measurement")

| Redbox Evaluation of the combined control and calibration zone | | | |
|---|---|---|---|
| Membrane No | | 29 (6/9/9) | |
| Concentration TnT [ng/ml] | 0 | 0.1 | 10 |
| Number [n] | 5 | 5 | 5 |
| Mean | 2044 | 2032 | 2044 |
| Standard deviation | 18.4 | 54.3 | 42.6 |
| CV | 0.9% | 2.7% | 2.1% |
| Linosbox 1 Evaluation of the combined control and calibration zone | | | |
| Membrane No | | 29 (6/9/9) | |
| Concentration TnT [ng/ml] | 0 | 0.1 | 10 |
| Number [n] | 5 | 5 | 5 |
| Mean | 53988 | 53945 | 54044 |
| Standard deviation | 553.1 | 1248.5 | 969.6 |
| CV | 1.0% | 2.3% | 1.8% |

Concentration TnT [ng/ml]: Concentration of troponin T in the sample which was analysed on the same test carrier after the dry measurement.
Number [n]: number of measurements carried out.
CV: coefficient of variation; standard deviation/mean in percent.

Subsequently the signal in the analyte detection zone was measured with the three samples in each case under the conditions of the Redbox and the Linosbox 1. For this purpose 40 µl in each case was pipetted into the sample application opening (4) of the test element and drawn by capillary forces into the primary channel section (5). After the reagents (6) (7) present in the primary channel section (5) were dissolved by the sample after incubation, the solution was transferred by centrifugation into the measuring chamber (12) containing the porous matrix (13) and the solid blood components were separated in the adjoining erythrocyte collection zone (11). The plasma/reagent mixture that was formed was chromatographed across the porous matrix (13) in a capillary manner by reducing the centrifugal force, where the analyte was then immobilized in the analyte detection zone (14). Excess fluorophore was removed from the membrane in the same way before the measurement by washing with washing buffer.

The signal in the analyte detection zone was determined in the Redbox and the Linosbox 1 after excitation with radiation of an excitation wavelength of 633 nm (see "mean" in Table 2). As expected the signal strengths of the samples containing troponin T are significantly increased compared to the background signal of the negative control (conc. TnT 0 ng/ml) due to the analyte-dependency of the signal. Also the relation between the signal strengths of the samples correspond to the troponin T concentrations that were used i.e. about 100-fold stronger signal at a 100-fold higher concentration. However, comparison of the absolute values between the Redbox and the Linosbox 1 experimental conditions showed a deviation of a factor of more than 20 (compare line "mean" Redbox and line "mean" Linosbox 1 in table 2). A calibrated measurement signal which only differs slightly between the two experimental conditions (see Table 2, line "correction") is only obtained by relating the signal determined previously in the combined control and calibration zone to the signal determined in the analyte detection zone according to the invention.

TABLE 2

Determination of the signal in the analyte detection zone after application of the sample to the test element

| Redbox Evaluation of the analyte detection zone | | | |
|---|---|---|---|
| Membrane No | | 29 (6/9/9) | |
| Concentration TnT [ng/ml] | 0 | 0.1 | 10 |
| Number [n] | 5 | 5 | 5 |
| Mean | 18 | 101 | 10612 |
| Standard deviation | 2.1 | 3.2 | 178.9 |
| CV | 11.9% | 3.2% | 1.7% |
| correction | $18/2044 = 8.8 \cdot 10^{-3}$ | $101/2032 = 49.7 \cdot 10^{-3}$ | $10612/2044 = 5.19$ |
| Linosbox 1 Evaluation of the analyte detection zone | | | |
| Membrane No | | 29 (6/9/9) | |
| Concentration TnT [ng/ml] | 0 | 0.1 | 10 |
| Number [n] | 5 | 7 | 5 |
| Mean | 361 | 2146 | 249298 |
| Standard deviation | 27 | 71 | 5310 |
| CV | 7.4% | 3.3% | 2.1% |
| correction | $361/53968 = 6.7 \cdot 10^{-3}$ | $2146/53945 = 39.7 \cdot 10^{-3}$ | $249298/54044 = 4.61$ |

Concentration TnT [ng/ml]: Concentration of troponin T in the sample.
Number [n]: number of measurements carried out.
CV: coefficient of variation; standard deviation/mean in percent.

All patents and patent applications identified herein are incorporated by reference in their entireties. Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

The invention claimed is:

1. A test element for conducting a specific binding assay, the element comprising an analyte detection zone and a combined control and calibration zone, wherein the combined control and calibration zone comprises a mixture of an immobilized fluorophore and an immobilized binding partner for the specific binding of a reagent labelled with a fluorophore.

2. The test element of claim 1, wherein the specific binding assay is an immunological sandwich assay.

3. The test element of claim 1, wherein the fluorophore in the combined control and calibration zone and the fluorophore of the reagent labelled with a fluorophore are excited at the same wavelength and emit electromagnetic radiation of the same wavelength.

4. The test element of claim 1, wherein the test element is an immunological chromatographic test strip.

5. The test element of claim 1, wherein the test element is a microarray.

6. The test element of claim 1, wherein the amount of the fluorophore in the combined control and calibration zone is between 0.001 µg and 5 µg, and the amount of binding partner in the control and calibration zone is between 1 ng and 500 ng.

7. A method for calibrating an analyte-specific measurement with the test element of claim 1 and an analyzer suitable for evaluating the test element, the method comprising:
 a) generating a signal in the combined control and calibration zone by exciting the fluorophore in the combined control and calibration zone in the absence of the reagent labelled with a fluorophore,
 b) measuring the signal generated in step a),
 c) contacting the sample with the test element and with the reagent labelled with a fluorophore so that the analyte, if present in the sample, results in a detectable signal in the analyte detection zone;
 d) generating a signal in the analyte detection zone by exciting the fluorophore of the reagent labelled with a fluorophore present in the analyte detection zone in the presence of the analyte,
 e) measuring the signal generated in step d),
 f) relating the signals measured in steps b) and e).

8. The method of claim 7, wherein the signals measured in steps b) and e) are offset against one another.

9. The method of claim 7, wherein the generation of a signal in the combined control and calibration zone by excitation of the fluorophore in the combined control and calibration zone in the absence of the reagent labelled with a fluorophore (step a)) and the measurement of the signal generated by the fluorophore (step b)) take place before the sample has been contacted with the test element and with the reagent labelled with a fluorophore (step c)).

10. A method for determining the concentration of an analyte in a sample with the test of claim 1 and suitable analyzer for evaluating the test element, the method comprising:
 a) generating a signal in the combined control and calibration zone by exciting the fluorophore in the combined control and calibration zone in the absence of the reagent labelled with a fluorophore,
 b) measuring the signal generated in step a),
 c) contacting the sample with the test element and with the reagent labelled with a fluorophore so that the analyte, if present in the sample, leads to a detectable signal in the analyte detection zone;
 d) generating a signal in the analyte detection zone by exciting the fluorophore of the reagent labelled with a fluorophore present in the analyte detection zone in the presence of the analyte,
 e) measuring the signal generated in step d),
 f) relating the signals measured in steps b) and e),
 g) comparing the relationship from step f) with a calibration curve,
 h) determining the concentration of the analyte on the basis of the comparison carried out in step g).

11. The method of claim 10, wherein the signals measured in steps b) and e) are offset against one another.

12. The method of claim 11, wherein the generation of a signal in the combined control and calibration zone by excitation of the fluorophore in the combined control and calibration zone in the absence of the reagent labelled with a fluorophore (step a)) and the measurement of the signal generated by the fluorophore (step b)) take place before the sample has been contacted with the test element and with the reagent labelled with a fluorophore (step c)).

* * * * *